United States Patent
Inagaki et al.

(10) Patent No.: US 6,653,034 B2
(45) Date of Patent: Nov. 25, 2003

(54) STILBENEAMINE DERIVATIVE AND ELECTROPHOTOSENSITIVE MATERIAL USING THE SAME

(75) Inventors: Yoshio Inagaki, Osaka (JP); Daisuke Kuboshima, Osaka (JP)

(73) Assignee: Kyocera Mita Corporation, Osaka (JP)

( * ) Notice: Subject to any disclaimer, the term of this patent is extended or adjusted under 35 U.S.C. 154(b) by 0 days.

(21) Appl. No.: 10/040,445

(22) Filed: Jan. 9, 2002

(65) Prior Publication Data

US 2002/0172877 A1 Nov. 21, 2002

(30) Foreign Application Priority Data

Mar. 21, 2001 (JP) ........................................ 2001-080513

(51) Int. Cl.$^7$ ...................... G03G 5/047; C07D 333/12
(52) U.S. Cl. ........................ 430/58.15; 430/75; 549/74
(58) Field of Search ................ 430/58.15, 75; 549/74

(56) References Cited

U.S. PATENT DOCUMENTS 5,215,842 A  *  6/1993  Aratani et al. ........... 430/58.15

FOREIGN PATENT DOCUMENTS

| JP | 58-123542 | 7/1983 |
| JP | 2-12256 | 1/1990 |
| JP | 9-134021 | 5/1997 |

OTHER PUBLICATIONS

European Search Report dated Apr. 17, 2002 (EP 02 25 0695).
Patent Abstracts of Japan, vol. 1997, No. 09, Sep. 30, 1997 & JP 09 134021, May 20, 1997 *Abstract*.
Patent Abstracts of Japan, vol. 014, No. 153 Mar. 23, 1990 & JP 02 012256, Jan. 17, 1990 *Abstract*.
Patent Abstracts of Japan, vol. 007, No. 238 Oct. 22, 1983 & JP 58 123542, Jul. 22, 1983 *Abstract*.

* cited by examiner

Primary Examiner—John Goodrow
(74) Attorney, Agent, or Firm—Smith, Gambrell & Russell LLP (57) ABSTRACT

The present invention relates to a stilbeneamine derivative represented by a formula (1):

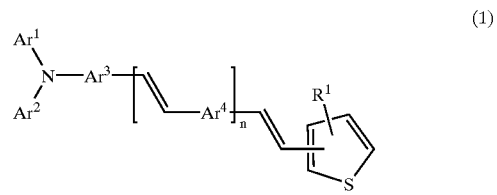

wherein $Ar^1$ and $Ar^2$ each denote an aryl group; $Ar^3$ denotes an arylene group; $Ar^4$ denotes an arylene group or divalent heterocyclic group; provided that when a thiophene ring in the formula is 2-thiophenyl, 'n' is 1 and when the thiophene ring is 3-thiophenyl, 'n' is 0 or 1, and also relates to an electrophotosensitive material comprising a photosensitive layer containing this derivative. The derivative is excellent in electric charge transferring capability, compatibility with a binder resin and stability, thus offering the electrophotosensitive material superior to the prior-art products in sensitivity and repeatability.

6 Claims, 3 Drawing Sheets

STILBENEAMINE DERIVATIVE AND ELECTROPHOTOSENSITIVE MATERIAL USING THE SAME

TECHNICAL FIELD

The present invention relates to a novel stilbeneamine derivative and an electrophotosensitive material using the same.

BACKGROUND OF THE INVENTION

As an electrophotosensitive material for use in image forming apparatuses such as electrostatic copiers, laser beam printers, plain paper facsimiles and the like, a so-called organic electrophotosensitive material is widespread which comprises a combination of the following components:

- a charge generating material for generating an electric charge (positive hole and electron) when exposed to light;
- a charge transport material for transporting the generated electric charge; and
- a binder resin.

The charge transport materials fall into two broad categories which include a positive-hole transport material for transporting positive holes of the electric charge, and an electron transport material for transporting electrons.

The organic electrophotosensitive material has an advantage over an inorganic electrophotosensitive material employing an inorganic semiconductor material in that the organic electrophotosensitive material is fabricated more easily at less production costs than the latter.

In addition, the organic electrophotosensitive material also has a merit of greater freedom of function design by virtue of a wide variety of options for materials including charge generating materials, charge transport materials, binder resins and the like.

In this connection, the organic electrophotosensitive materials have recently been widely used in the image forming apparatuses.

Unfortunately, however, the organic electrophotosensitive materials are inferior to the inorganic electrophotosensitive materials in photosensitivity and in electrical stability in the course of repeated image forming cycles, or in other words, repeatability.

With an aim at solving the above problem, intensive study has been made on the improvement of various materials for use in the organic electrophotosensitive materials. The charge transport material, in particular, is an important material affecting not only the sensitivity but also the repeatability of the electrophotosensitive material.

Japanese Laid-open Patent Publication JP 02-12256 A (1990) discloses a charge transport material of stilbeneamine derivative represented by a formula (2):

wherein $Ar_1$ denotes an aryl group or heterocyclic group, each optionally having a substituent; $Ar_2$ and $Ar_3$ are the same or different, each denoting an arylene group; and $R_1$ and $R_2$ each denote an alkyl group, aralkyl group or aryl group, each optionally having a substituent; provided that $Ar_3$ and $R_1$ or $Ar_3$, $R_1$ and $R_2$ may be combined together to form a heterocycle. Incidentally, the patent publication cites quinolyl, carbazolyl, oxazolyl and imidazolyl as the heterocyclic group represented by $Ar_1$.

Alternatively, Japanese Laid-open Patent Publication JP 58-123542 A (1983) discloses a stilbeneamine derivative which is represented by a formula (3):

wherein $X_1$ and $X_2$ are the same or different, each denoting a phenyl group optionally having a substituent; $X_3$ denotes an arylene group optionally having a substituent; and $X_4$ denotes an aryl group, 2-furil group, or 2-thienyl group, each optionally having a substituent.

There is further disclosed in Japanese Laid-open Patent publication JP 09-134021 A (1997) a stilbeneamine derivative represented by a formula (4):

wherein $R^a$, $R^b$, $R^c$, $R^d$ and $R^e$ each denote a hydrogen atom, halogen atom, alkyl group, aryl group or alkoxy group; and x denotes an integer of 0 to 2.

However, the inventors have examined the stilbeneamine derivatives disclosed in the above official gazettes to find that all these compounds suffer the following problems:

- that they still fall short of achieving sufficient compatibility with the binder resin to be uniformly dispersed in the photosensitive layer, thus suffering a low tendency of producing electric charge transfer;
- that they are still short of electric charge transferring capability;
- that they suffer insufficient in electrical, physical and chemical stabilities; and
- that as a consequence, the electrophotosensitive materials comprising these compounds are not only sufficiently improved in photosensitivity but also suffer poor repeatability.

SUMMARY OF THE INVENTION

It is an object of the invention to provide a novel stilbeneamine derivative which has a larger electric charge mobility than the prior-art compounds, thus featuring excellent electric charge transferring capability and which is also excellent in compatibility with the binder resin and in stability.

It is another object of the invention to provide an electrophotosensitive material using the above stilbeneamine derivative and featuring excellent sensitivity and repeatability.

For achieving the above objects, the inventors have conducted analysis on the structure of a stilbeneamine derivative represented by a formula (1):

(1)

wherein $R^1$ denotes an alkyl group, alkoxy group, aryl group, aralkyl group, halogen atom or hydrogen atom; $Ar^1$ and $Ar^2$ are the same or different, each denoting an aryl group; $Ar^3$ denotes an arylene group; and $Ar^4$ denotes an arylene group or divalent heterocyclic group.

Finally, the inventors have discovered that the above objects can be achieved by limiting In, in the formula to 1 when a terminal thiophene ring of the stilbeneamine derivative is 2-thienyl or by limiting 'n' to 0 or 1 when the terminal thiophene ring is 3-thienyl.

That is, the stilbeneamine derivative of the invention is represented by the formula (1):
wherein $R^1$ denotes an alkyl group, alkoxy group, aryl group, aralkyl group, halogen atom or hydrogen atom; $Ar^1$ and $Ar^2$ are the same or different, each denoting an aryl group; $Ar^3$ denotes an arylene group; and $Ar^4$ denotes an arylene group or divalent heterocyclic group; provided that when a thiophene ring in the formula is 2-thienyl, 'n' is 1 whereas when the thiophene ring is 3-thienyl, 'n' is 0 or 1.

The stilbeneamine derivative represented by the formula (1) is absolutely a novel compound which is not specifically described in any of the above official gazettes.

If the stilbeneamine derivative of the formula (1) is compared with a compound represented by the formula (2) and defined as $Ar^1$ being an aryl group such as a phenyl group, the former is more improved in compatibility with the binder resin than the latter. This is because the thienyl group has a higher degree of asymmetry in terms of molecular structure and electrical property than the aryl group.

The thienyl group has a higher electron donatability than the aryl group and the other heterocyclic groups (such as the aforesaid quinolyl, carbazolyl, oxazolyl, imidazolyl and the like). Thus, the stilbeneamine derivative of the formula (1) is superior to the compounds of the formula (2) in electric charge transferring capability, as well.

If, out of the stilbeneamine derivatives of the formula (1), a compound having 3-thienyl group as the thiophene ring and defined as 'n' being 0 is compared with a compound represented by the formula (3) and having 2-thienyl group as $X_4$ or a compound represented by the formula (4) and defined as 'x' being 0, the former has a larger ionization potential than the latter ones. Thus, the former stilbeneamine derivative is particularly more improved in electrical stability than the latter compounds.

If, out of the stilbeneamine derivatives of the formula (1), a compound having 2-thienyl group or 3-thienyl group as the thiophene ring and defined as 'n' being 1 is compared with the compound of the formula (3), the former has a larger spread of π-electron conjugated system than the latter because of the presence of —CH═CH—$Ar^4$— at the molecular center. Thus, the former stilbeneamine derivative is superior to the compound of the formula (3) in electric charge transferring capability. Furthermore, the former stilbeneamine derivative is more excellent in stability than the latter, because of the greater molecular weight of the basic skeleton.

If, out of the stilbeneamine derivatives of the formula (1), the compound having 2-thienyl group or 3-thienyl group as the thiophene ring and defined as 'n' being 1 is compared with a compound represented by the formula (4) and defined as 'x' being 1 or 2, the former has a larger spread of π-electron conjugated system than the latter. Thus, the former stilbeneamine derivative is superior to the latter compounds in electric charge transferring capability. Furthermore, the former stilbeneamine derivative is more excellent in stability than the latter, because of the greater molecular weight of the basic skeleton.

When all these facts considered, the inventive stilbeneamine derivative represented by the formula (1) is superior to the prior-art compounds represented by the formulas (2) to(4) incompatibility with binder resin, electric charge transferring capability and stability.

The electrophotosensitive material according to the invention comprises a photosensitive layer formed on a conductive substrate and containing the stilbeneamine derivative of the formula (1) as a hole transport material.

The electrophotosensitive material of the invention comprises the photosensitive layer containing therein, as the hole transport material, the stilbeneamine derivative of the formula (1) which, as mentioned supra, is excellent in electrical charge transferring capability and compatibility with the binder resin. Accordingly, the inventive electrophotosensitive material has a great rate of transferring electric charges (holes) generated in the charge generating material or a large electric charge mobility, thus featuring high photosensitivity when exposed to light. The large electric charge mobility contributes to a great drop of residual potential after light exposure. As combined results of this feature and the high stability of the stilbeneamine derivative, the electrophotosensitive material of the invention has an excellent repeatability.

DETAILED DESCRIPTION OF THE INVENTION

The present invention will hereinbelow be described in detail.

First, the inventive stilbeneamine derivative represented by the formula (1) is described.

Examples of a suitable alkyl group represented by $R^1$ in the formula include alkyl groups having 1 to 6 carbon atoms, such as methyl, ethyl, n-propyl, isopropyl, n-butyl, isobutyl, s-butyl, t-butyl, pentyl, isopentyl, neopentyl, hexyl and the like. Above all, particularly preferred are alkyl groups having 1 to 4 carbon atoms, such as methyl, ethyl, n-propyl, isopropyl, n-butyl, isobutyl, s-butyl, t-butyl and the like.

Examples of a suitable alkoxy group include alkoxy groups having 1 to 6 carbon atoms, such as methoxy, ethoxy, propoxy, isopropoxy, butoxy, t-butoxy, pentyloxy, hexyloxy and the like.

Examples of a suitable aryl group include aryl groups having 6 to 14 carbon atoms, such as phenyl, tolyl, xylyl, biphenylyl, o-terphenylyl, naphthyl, anthryl, phenanthryl and the like.

Examples of a suitable aralkyl group include aralkyl groups having 1 to 6 carbon atoms in the alkyl moiety or 6 to 14 carbon atoms in the aryl moiety, such as benzyl, benzhydryl, trityl, phenethyl, 1-phenylethyl, 3-phenylpropyl, 4-phenylbutyl, 5-phenylpentyl, 6-phenylhexyl and the like.

The above alkyl group, alkoxy group, aryl group and aralkyl group may optionally have a substituent.

Examples of a suitable substituent include hydroxyalkyl group, alkoxyalkyl group, monoalkylaminoalkyl group, dialkylaminoalkyl group, halogenated alkyl group, alkoxycarbonylalkyl group, carboxyalkyl group, alkanoyloxyalkyl group, aminoalkyl group, halogen atoms, amino group, hydroxy group, optionally esterified carboxyl group, cyano group and the like. Furthermore, the aforesaid alkyl groups having 1 to 6 carbon atoms and alkoxy groups having 1 to 6 carbon atoms are also usable. It is noted that the substituents for the alkyl group, alkoxy group, aryl group and aralkyl group are not particularly limited in the position or the number. Furthermore, the substituents may optionally have a substituent.

Examples of a suitable halogen atom represented by $R^1$ include fluorine, chlorine, bromine, iodine and the like.

Examples of a suitable aryl group represented by $Ar^1$ or $Ar^2$ include monovalent groups derived from aromatic rings having 6 to 14 carbon atoms, such as benzene ring, naphthalene ring, anthracene ring, phenanthrene ring, fluorene ring and the like.

Likewise, examples of a suitable arylene group represented by $Ar^3$ or $Ar^4$ include divalent groups derived from aromatic rings having 6 to 14 carbon atoms, such as benzene ring, naphthalene ring, anthracene ring, phenanthrene ring, fluorene ring and the like.

Examples of a divalent heterocyclic group represented by $Ar^4$ include divalent groups derived from heterocycles such as furan, thiophene, quinoline, carbazole, oxazole, imidazole and the like. Particularly preferred is a divalent group derived from thiophene ring.

The above aryl group, arylene group and divalent heterocyclic group may optionally have a substituent. Examples of a suitable substituent include the same as those for the group $R^1$. It is noted that the substituents for the aryl group, arylene group and divalent heterocyclic group are not particularly limited in the position or the number. Furthermore, the substituents may optionally have a substituent.

The two bonds of the arylene group may be at any of the ortho, meta and para positions. The two bonds of the divalent heterocyclic group may be at any positions.

As mentioned supra, 'n' in the formula (1) is defined as 1 when the thiophene ring is 2-thienyl and as 0 or 1 when the thiophene ring is 3-thienyl. Accordingly, the stilbeneamine derivative of the formula (1) includes the following three compounds represented by formulas (11) to (13). It is noted that the symbols in the formulas are as defined in the foregoing.

(11)

(12)

(13)

Specific examples of the compound of the formula (11) include the following compounds represented by formulas (11-1) to (11-27).

(11-1)

(11-2)

(11-3)

(11-4)

(11-5)

(11-6)
(11-7)
(11-8)
(11-9)

(11-10)
(11-11)

(11-12)

(11-13)
(11-14)

(11-15)

(11-21)

(11-16)
(11-22)

(11-17)
(11-23)

(11-18)
(11-24)

(11-19)
(11-25)

(11-20)

(11-26)

(11-27)

Specific examples of the compound of the formula (12) include the following compounds represented by formulas (12-1) to (12-27).

(12-1)

(12-2)

(12-3)

(12-4)

(12-5)

(12-6)

(12-7)

(12-8)

(12-9)

(12-10)

-continued

(12-11)
(12-12)
(12-13)
(12-14)
(12-15)

-continued

(12-16)
(12-17)
(12-18)
(12-19)
(12-20)
(12-21)

(12-22)

(12-27)

(12-23)

Specific examples of the compound of the formula (13) include the following compounds represented by formulas (13-1) to (13-15).

(13-1)

(12-24)

(13-2)

(12-25)

(13-3)

(12-26)

(13-4)

(13-5)

(13-6)

(13-7)

(13-8)

(13-9)

(13-10)

(13-11)

(13-12)

(13-13)

(13-14)

-continued (13-15)

The stilbeneamine derivative (1) of the invention can be synthesized by performing a reaction represented by Reaction Scheme (I):

wherein the symbols are as defined in the foregoing.

In this scheme, phosphostilbeneamine derivative represented by a general formula (5) is reacted with formylated thiophene represented by a general formula (6) in a suitable anhydrous solvent in the presence of a base, thereby giving the stilbeneamine derivative represented by the general formula (1).

The anhydrous solvent used in the above reaction may be any one that does not affect the reaction. Examples of a suitable anhydrous solvent include ethers such as diethyl ether, tetrahydrofuran, dioxane and the like; halogenated hydrocarbons such as methylene chloride, chloroform, dichloroethane and the like; and aromatic hydrocarbons such as benzene, toluene and the like.

Examples of a usable base include sodium alkoxide such as sodium methoxide, and metal hydride such as sodium hydride.

The amount of the phosphostilbeneamine derivative (5) is from 0.90 to 2.05 times, or preferably from 0.98 to 1.25 times, in a molar ratio per mol of the formylated thiophene (6).

The amount of the base is at least one time, or preferably from 1 to 1.3 times, in a molar ratio per mol of the formulated thiophene (6). The reaction is normally performed at −10 to 25° C. and is completed within the range of about 3 to 12 hours.

The phosphostilbeneamine derivative (5) as a starting material of the above reaction maybe synthesized by performing a reaction represented by Re action Scheme (II):

wherein X denotes a halogen atom and the other symbols are as defined in the foregoing.

In this scheme, a halogenated methylstilbeneamine derivative (7) is reacted with triester phosphite (8) without solvent or in a suitable solvent, thereby giving a phosphostilbeneamine derivative (5). The reaction will be promoted if tertiary amine is added to remove a halogenated alkyl from the reaction system.

The solvent used in this reaction may be any one that does not affect the reaction. Examples of a usable solvent include ethers such as diethyl ether, tetrahydrofuran, dioxane and the like; halogenated hydrocarbons such as methylene chloride, chloroform, dichloroethane and the like; and aromatic hydrocarbons such as benzene, toluene and the like; and dimethylformamide and the like.

Examples of a usable tertiary amine in the reaction system include triethylamine, tributylamine, pyridine, 4-(dimethylamino)pyridine and the like.

The amount of the triester phosphite (8) is at least one time, or preferably from 1 to 1.2 times, in molar ratio per mol of the halogenated methylstilbeneamine derivative (7). The reaction is normally performed at 80 to 150° C. and is completed within the range of about 1 to 4 hours.

Next, the electrophotosensitive material according to the invention will be described.

The electrophotosensitive material of the invention comprises a photosensitive layer formed on a conductive substrate and containing at least one of the stilbeneamine derivatives represented by the formula (1). As is well known in the art, the photosensitive layer includes a single-layer type and a multi-layer type, to both of which the construction of the invention is applicable.

The single-layer photosensitive layer is formed by the steps of applying a coating solution to the conductive substrate and drying the solution, the coating solution prepared by dissolving or dispersing in a suitable solvent at least one of the stilbene derivatives (1) as the hole transport material, a charge generating material, a binder resin and, if required, an electron transport material.

The single-layer photosensitive layer features a simple layer construction and good productivity.

In addition, the single-layer photosensitive layer employing charge transport materials of opposite polarities is advantageous in that the single layer construction is positively and negatively charge able.

The electrophotosensitive material of the invention having the single-layer photosensitive layer achieves greater drop of residual potential and improvement of photosensitivity and repeatability, as compared with the electrophotosensitive materials having the single-layer photosensitive layer comprising the prior-art stilbenamine derivatives as the hole transport material.

On the other hand, the multi-layer photosensitive layer is formed by the steps of overlaying, on the conductive substrate, the charge generating layer containing the charge generating material by a known method such as vapor deposition or solution coating, applying thereto a coating solution containing at least one of the stilbeneamine derivatives (1) as the hole transport material and the binder resin, and drying the solution thereby to form the charge transport layer.

Otherwise, the multi-layer photosensitive layer may also be obtained by forming the charge transport layer over the conductive substrate, followed by forming thereover the charge generating layer.

However, the charge generating layer has a much smaller film thickness than the charge transport layer. From the standpoint of protecting the charge generating layer, therefore, it is preferred to form the charge generating layer on the conductive substrate and then to overlay the charge transport layer thereon.

The charging type (positive or negative) of the multi-layer photosensitive layer is selected based on the order of formation of the charge generating layer and the charge transport layer as well as on the type of the charge transport material used in the charge transport layer. For instance, if the above procedure including the steps of forming the charge generating layer on the conductive substrate and then laying thereover the charge transport layer containing the stilbeneamine derivative (1) as the hole transport material is taken, the resultant photosensitive layer is of the negatively charged type.

The electrophotosensitive material of the invention having the multi-layer photosensitive layer achieves greater drop of residual potential and improvement of photosensitivity and repeatability, as compared with the electrophotosensitive materials having the multi-layer photosensitive layer comprising the prior-art stilbeneamine derivatives as the hole transport material.

As mentioned supra, the construction of the invention is applicable to both the single-layer and multi-layer photosensitive layers. However, the invention may be more preferably applied to the single-layer photosensitive layer in the light of the positive/negative charge ability, the simple construction which is easy to fabricate, the suppression of occurrence of film failure in the film forming process and the improvement of optical characteristics because of small interlaminar surface.

A variety of materials for use in the electrophotosensitive material of the invention will be described below.

Examples of a usable charge generating material include powders of inorganic photoconductive materials such as selenium, selenium-tellurium, selenium-arsenic, cadmium sulfide, amorphous silicon, amorphous carbon and the like; and a variety of known pigments including phthalocyanine pigments comprising crystalline phthalocyanine compounds of various crystalline forms such as metal-free phthalocyanine represented by a formula (CG-1):

(CG-1)

titanyl phthalocyanine represented by a formula (CG-2);

(CG-2)

azo pigments, bisazo pigments, perylene pigments, anthanthrone pigments, indigo pigments, triphenylmethane pigments, threne pigments, toluidine pigments, pyrazoline pigments, quinacridone pigments, dithioketopyrolopyrrole pigments and the like.

The charge generating materials may be used alone or in combination of two or more types such that the photosensitive layer may have sensitivity at a desired wavelength range.

Particularly, an electrophotosensitive material having photosensitivity in the wavelength range of 700 nm or more is required by digital-optical image forming apparatuses such as laser beam printers, plain paper facsimiles and the like which utilize infrared light such as semiconductor laser beam. The refore, out of the above exemplary compounds, phthalocyanine pigments are preferably employed as the charge generating material.

Any of the various known electron transportable compounds may be used as the electron transport material.

A particularly preferred electron transport material includes electron-attracting compounds which include, benzoquinone compounds, diphenoquinone compounds (e.g., 2,6-dimethyl-2',6'-t-butylbenzoquinone), naphthoquinone compounds, malononitrile, thiopyran compounds, tetracyanoethylene, 2,4,8-trinitrothioxanthone, fluorenone compounds (e.g., 2,4,7-trinitrilo-9-fluorenone), dinitrobenzene, dinitroanthracene, dinitroacridine, nitroanthraquinone, succinic anhydride, maleic anhydride, dibromomaleic anhydride, 2,4,7-trinitrofluorenoneimine compounds, ethylated nitrofluorenoneimine compounds, tryptanthrin compounds, tryptanthrinimine compounds, azafluorenone compounds, dinitropyridoquinazoline compounds, thioxanthene compounds, 2-phenyl-1,4-benzoquinone compounds, 2-phenyl-1,4-naphthoquinone compounds, 5,12-naphthacenequinone compounds, α-cyanostilbene compounds, 4'-nitrostilbene compounds, salts formed by reaction between anionic radicals of benzoquinone compounds and cations.

These materials may be used alone or in combination of two or more types.

According to the invention, the stilbeneamine derivative of the formula (1) as the hole transport material may be used in combination with another hole transport material.

Any of the various known hole transportable compounds may be used as the additional hole transport material.

Examples of a suitable hole transport material include benzidine compounds, phenylenediamine compounds, naphthylenediamine compounds, phenanthrylenediamine compounds, oxadiazole compounds (i.g., 2,5-di(4-methylaminophenyl)-1,3,4-oxadiazole), styryl compounds (i.g., 9-(4-diethylaminostyryl)anthracene), carbazole compounds (i.g., poly-N-vinylcarbazole), organicpolysilane compounds,pyrazoline compounds(i.g., 1-phenyl-3-(p-dimethylaminophenyl)pyrazoline), hydrazone compounds (i.g., diethylaminobenzaldehyde diphenylhydrazone), triphenylamine compounds (i.g., tris(3-methylphenyl)amine), indole compounds, oxazole compounds, isoxazole compounds, thiazole compounds, thiadiazole compounds, imidazole compounds, pyrazole compounds, triazole compounds, butadiene compounds, pyrene-hydrazone compounds, acrolein compounds, carbazole-hydrazone compounds, quinoline-hydrazone compounds, stilbene-hydrazone compounds, diphenylenediamine compounds and the like.

These compounds may be used alone or in combination of two or more types.

Examples of a usable binder resin include thermoplastic resins such as styrene polymers, styrene-butadiene copolymers, styrene-acrylonitrile copolymers, styrene-maleic acid copolymers, acrylic polymers, styrene-acryl copolymers, polyethylene, ethylene-vinyl acetate copolymers, chlorinated polyethylene, polyvinyl chloride, polypropylene, copolymers of vinyl chloride and vinyl acetate, polyester, alkyd resins, polyamide, polyurethane, polycarbonate, polyarylate, polysulfone, diarylphthalate resins, ketone resins, polyvinylbutyral resins, polyether resins and the like; thermosetting resins such as silicone resins, epoxy resins, phenol resins, urea resins, melamine resins and other crosslinking thermosetting resins; and photosetting resins such as epoxy-acrylate, urethane-acrylate and the like.

These resins may be used alone or in combination of two or more types.

Where a high-molecular hole transport material such as poly-N-vinylcarbazole or the organic polysilane compound described above is used in combination, the aforesaid binder resin may be dispensed with because such a compound also serves as the binder resin.

Additionally to the above components, the photosensitive layer may further contain any of the various additives such as a fluorene compound, ultraviolet absorber, plasticizer, surfactant, leveling agent and the like. For an increased sensitivity of the electrophotosensitive material, there may be further admixed a sensitizer such as terphenyl, halonaphthoquinone, acenaphthylene or the like.

The single-layer photosensitive layer may preferably contain 0.1 to 50 parts by weight or particularly 0.5 to 30 parts by weight of charge generating material, and 5 to 500 parts by weight or particularly 25 to 200 parts by weight of hole transport material, based on 100 parts by weight of binder resin.

Where the stilbeneamine derivative of the formula (1) is used alone, the amount of the hole transport material means that of the stilbeneamine derivative. Where the stilbeneamine derivative is used in combination with another hole transport material, the amount of the hole transport material means the total amount of the stilbeneamine derivative and the additional hole transport material.

Where the stilbeneamine derivative is used in combination with another hole transport material, the additional hole transport material may preferably be present in such a small amount that the aforesaid effect of the stilbeneamine derivative may not be decreased. More specifically, the additional hole transport material may be present in concentrations of not more than 30 parts by weight based on 100 parts by weight of stilbeneamine derivative.

Where the electron-transport material is used in combination with the stilbeneamine derivative, the electron-transport material may preferably be present in concentrations of 5 to 100 parts by weight or particularly 10 to 80 parts by weight based on 100 parts by weight of binder resin. In this case, the total amount of the hole transport material and the electron-transport material may preferably be in the range of 20 to 500 parts by weight or particularly 30 to 200 parts by weight based on 100 parts by weight of binder resin.

The single-layer photosensitive layer may preferably have a thickness of 5 to 100 $\mu$m or particularly of 10 to 50 $\mu$m.

The charge generating layer of the multi-layer photosensitive layer may be formed from the charge generating material alone or formed from the binder resin in which the charge generating material and, as required, the electron transport material are dispersed. In the latter case, it is preferred to use 5 to 1000 parts by weight or particularly 30 to 500 parts by weight of charge generating material and 1 to 200 parts by weight or particularly 5 to 100 parts by weight of electron transport material based on 100 parts by weight of binder resin.

The charge transport layer may preferably contain the hole transport material in concentrations of 10 to 500 parts by weight or particularly 25 to 200 parts by weight based on 100 parts by weight of binder resin.

Similarly to the single-layer photosensitive layer, the amount of the hole transport material means that of the stilbeneamine derivative of the formula (1) when the stilbeneamine derivative is used alone. Where the stilbeneamine derivative is used in combination with another hole transport material, the amount of the hole transport material means the total amount of the stilbeneamine derivative and the additional hole transport material.

Where the stilbeneamine derivative is used in combination with another hole transport material, the additional hole transport material may preferably be present in such a small amount that the aforesaid effect of the stilbeneamine derivative may not be decreased. More specifically, the additional hole transport material may be present in concentrations of not more than 30 parts by weight based on 100 parts by weight of stilbeneamine compound.

As to the thickness of the multi-layer photosensitive layer, the charge generating layer may preferably have a thickness of about 0.01 to 5 $\mu$m or particularly 0.1 to 3 $\mu$m, whereas the charge transport layer may preferably have a thickness of about 2 to 100 $\mu$m or particularly 5 to 50 $\mu$m.

An intermediate layer or barrier layer may be formed between the organic photosensitive layer of the single-layer type or multi-layer type and the conductive substrate or between the charge generating layer and the charge transport layer of the multi-layer photosensitive layer, so long as such a layer does not decrease the characteristics of the electrophotosensitive material.

Where each layer constituting the electrophotosensitive material is formed by the coating method, the charge generating material, charge transport material, and binder resin may be dispersed, by mixing, into an organic solvent using a roll mill, ball mill, attritor, paint shaker, ultrasonic disperser or the like, thereby to prepare a coating solution, which may be applied and dried by the known means.

Examples of a usable organic solvent include alcohols such as methanol, ethanol, isopropanol, butanol and the like;

aliphatic hydrocarbons such as n-hexane, octane, cyclohexane and the like; and aromatic hydrocarbons such as benzene, toluene, xylene and the like;

halogenated hydrocarbons such as dichloromethane, dichloroethane, carbon tetrachloride, chlorobenzene and the like;

ethers such as dimethyl ether, diethyl ether, tetrahydrofuran, 1,4-dioxane, ethyleneglycol dimethyl ether, diethyleneglycol dimethyl ether and the like;

ketones such as acetone, methyl ethyl ketone, cyclohexanone and the like;

esters such as ethyl acetate, methyl acetate and the like; and dimethylformaldehyde, dimethylformamide, dimethyl sulfoxide and the like. These solvents may be used alone or in combination of two or more types.

The coating solution may further contain a surfactant, leveling agent or the like for increasing the dispersibility of the charge generating material and charge transport material, and for the surface smoothness of the photosensitive layer.

The conductive substrate may employ any of those formed from various materials having conductivity. Examples of a usable conductive substrate include those formed from metals such as iron, aluminum, copper, tin, platinum, silver, vanadium, molybdenum, chromium, cadmium, titanium, nickel, palladium, indium, stainless steel, brass and the like; that formed from a plastic material on which any of the above metals is deposited or laminated; and a glass substrate coated with aluminum iodide, tin oxide, indium oxide or the like.

In short, the substrate itself may have the conductivity or the surface thereof may have the conductivity. It is preferred that the conductive substrate has a sufficient mechanical strength in use.

The conductive substrate may have any form, such as sheet, drum and the like, according to the construction of the image forming apparatus to which the conductive substrate is applied.

As described above, the invention contributes to the speed-up and high performance of the image forming apparatuses such as electrostatic copiers, laser beam printers, plain paper facsimiles and the like.

EXAMPLES

The invention will hereinbelow be described by way of reference to Synthesis Examples, Comparative Synthesis Examples, Examples and Comparative Examples thereof.

Synthesis Example 1

In a flask equipped with a Dean-Stark trap and reflux condenser, 0.016 mol (4.7 g) of 4-chloromethyl tripheny-lamine and 0.019 mol (3.2 g) of triethyl phosphite were reacted by stirring at 150 to 160° C. for 5 hours. After the completion of the reaction, the reaction solution was added in iced water and extracted with ethyl acetate. The resultant extract was washed with water, dried over anhydrous sodium sulfate, and then distilled away the solvent. The resultant product was purified by column chromatography (developing solvent: chloroform-hexane mixed solvent) to obtain 0.015 mol (5.9 g) of 4-phosphodiethyltriphenylamine.

Subsequently, a flask was charged with 0.015 mol (5.9 g) of 4-phosphodiethyltripheylamine, was degassed, and was replaced with argon. The n, 150 mL of anhydrous tetrahydrofuran was added and then, 0.017 mol (0.41 g) of sodium hydride was added dropwise with cooling in an ice bath. The mixture was subjected to two-hour stirring with temperature maintained at 0° C. At this temperature, 0.017 mol (2.1 g) of 3-formyl-4-methylthiophene in tetrahydrofuran was added dropwise to the mixture with stirring at temperatures ranging from 0° C. to room temperature. After the lapse of 3 hours, the reaction solution was added with water to terminate the reaction and was extracted with ethyl acetate. The reaction product was washed with water and the solvent was distilled off. The resultant product was purified by column chromatography (developing solvent: chloroform-hexane mixed solvent) to obtain 4.3 g of stilbeneamine derivative of the formula (12-2) (yield: 73%).

Synthesis Example 2

The same procedure as in Synthesis Example 1 was taken to obtain 0.015 mol (6.7 g) of N,N-(4-diethyl phosphate) diphenyl-1-naphthylamine, except that 0.016 mol (5.5 g) of N,N-(4-chloromethyl)diphenyl-1-naphthylamine was used instead of 4-chloromethyltriphenylamine.

Subsequently, the resultant compound was reacted with 0.017 mol (1.9 g) of 3-formylthiophene, instead of 3-formyl-4-methylthiophene, the same way as in Synthesis Example 1. Thus was obtained 5.2 g of stilbeneamine derivative of the formula (12-8) (yield: 80%).

Synthesis Example 3

The same procedure as in Synthesis Example 1 was taken to obtain 0.015 mol (6.4 g) of 4,4'-dimethyl-4"-phosphodiethyltriphenylamine, except that 0.016 mol (5.1 g) of 4-chloromethyl-4',4"-dimethyltriphenylamine was used instead of 4-chloromethyltriphenylamine.

Figure 1:
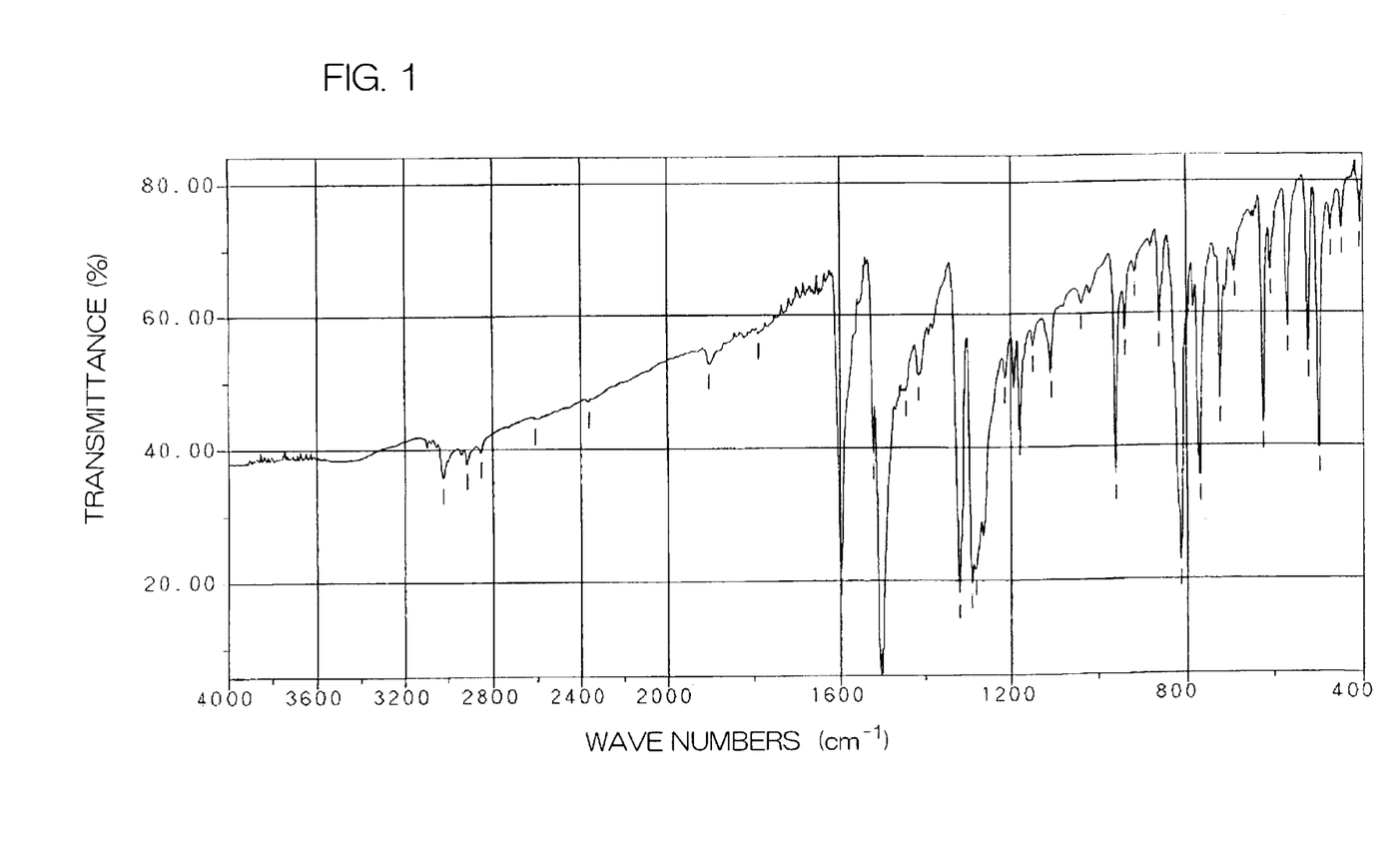
FIG. 1 is a graphical representation of the infrared absorption spectrum of a stilbeneamine derivative represented by a formula (12-15) and synthesized in Synthesis Example 3.

Subsequently, the resultant compound was reacted with 0.17 mol (1.9 g) of 3-formylthiophene, instead of 3-formyl-4-methylthiophene, the same way as in Synthesis Example 1. Thus was obtained 4.6 g of stilbeneamine derivative of the formula (12-15) (yield: 75%, melting point: 152° C.). The infrared absorption spectrum of the compound is shown in FIG. 1.

Synthesis Example 4

The same procedure as in Synthesis Example 1 was taken to obtain 0.0091 mol (5.0 g) of N,N-(4-phosphodiethylstyryl)diphenyl-1-naphthylamine, except that 0.0096 mol (4.3 g) of N,N-(4-chloromethylstyryl) diphenyl-1-naphthylamine was used instead of 4-chloromethyltriphenylamine and that the amount of triethyl phosphite was decreased to 0.012 mol (1.9 g).

Subsequently, the resultant compound was reacted the same way as in Synthesis Example 1, except that 0.011 mol (1.2 g) of 2-formylthiophene was used instead of 3-formyl- 4-methylthiophene and that the amount of sodium hydride was decreased to 0.011 mol (0.26 g). Thus was obtained 3.8 g of stilbeneamine derivative of the formula (11-6) (yield: 78%).

Synthesis Example 5

The same procedure as in Synthesis Example 4 was taken to obtain 0.0092 mol (5.0 g) of 4-phosphodiethylstyryl-2'-ethyl-6'-methylphenylaminie, except that 0.0096 mol (4.2 g) of 4-chloromethylstyryl-2'-ethyl-6'-methyltriphenylamine was used instead of N,N-(4-chloromethylstyryl)diphenyl-1-naphthylamine.

Figure 2:
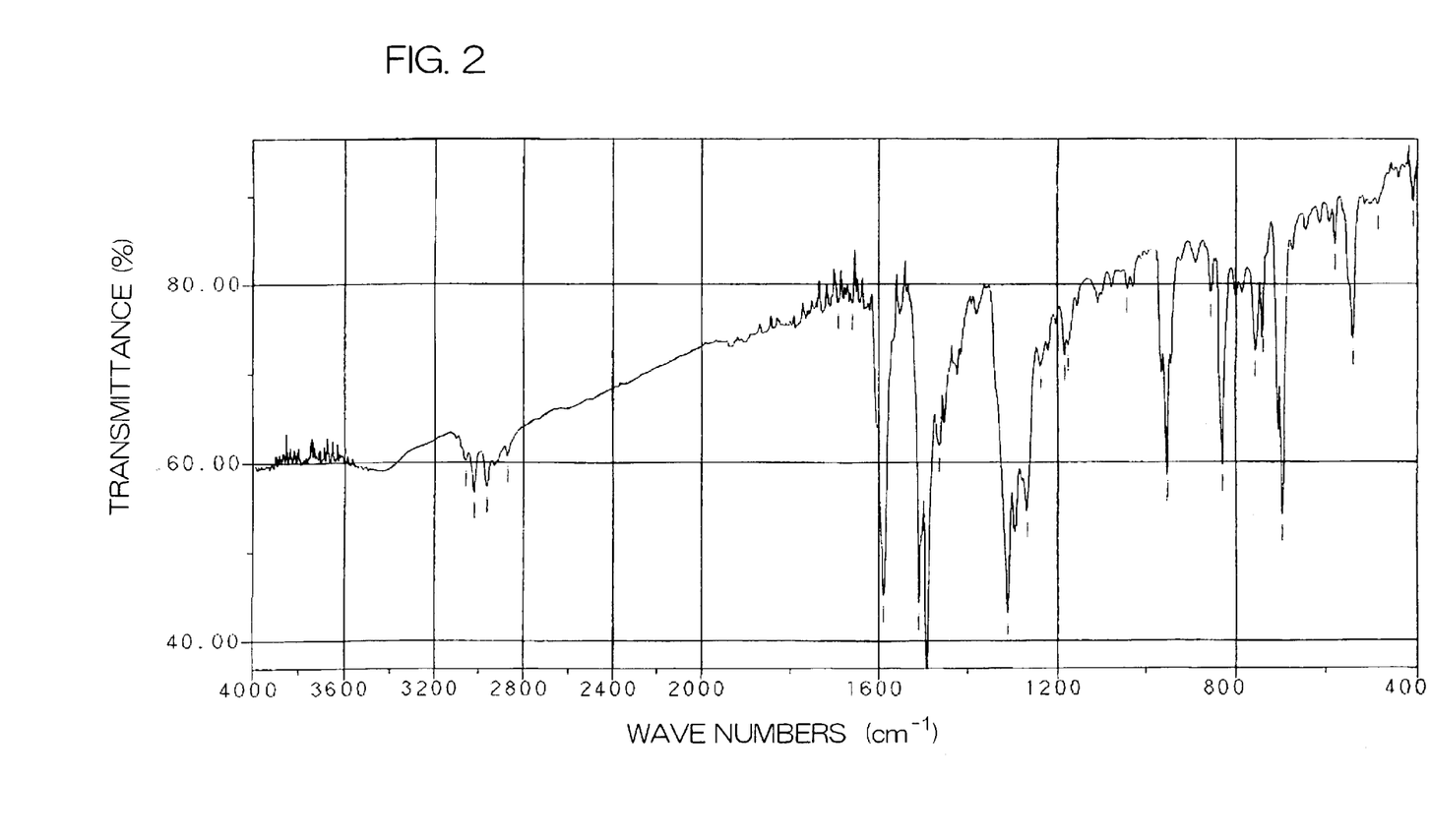
FIG. 2 is a graphical representation of the infrared absorption spectrum of a stilbeneamine derivative represented by a formula (11-7) and synthesized in Synthesis Example 5.

Subsequently, the resultant compound was reacted the same way as in Synthesis Example 4 to obtain 3.8 g of stilbeneamine derivative of the formula (11-7) (yield: 80%, melting point: 153° C.). The infrared absorption spectrum of the compound is shown in FIG. 2.

Synthesis Example 6

The same procedure as in Synthesis Example 4 was taken to obtain 0.0090 mol (5.3 g) of 4-phosphodiethylstyryl-2'-phenyl-6'-methyltriphenylamine, except that 0.0096 mol (4.7 g) of 4-chloromethylstyryl-2'-phenyl-6'-methyltriphenylamine was used instead of N,N-(4-chloromethylstyryl)diphenyl-1-naphthylamine.

Subsequently, the resultant compound was reacted the same way as in Synthesis Example 4 to obtain 4 g of stilbeneamine derivative of the formula (11-8) (yield: 77%).

Synthesis Example 7

Figure 3:
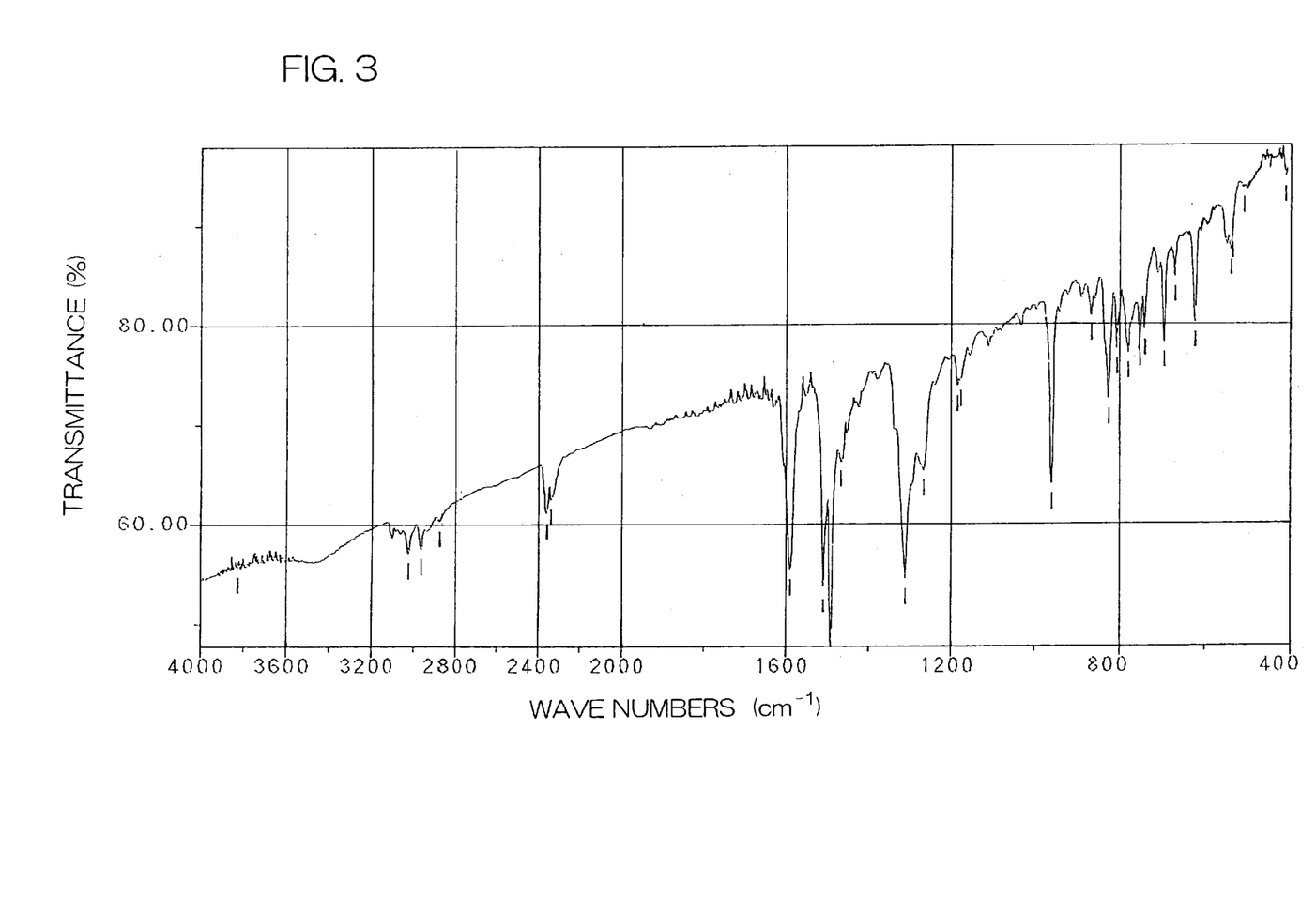
FIG. 3 is a graphical representation of the infrared absorption spectrum of a stilbeneamine derivative represented by a formula (13-15) and synthesized in Synthesis Example 7.

The same procedure as in Synthesis Example 5 was taken to obtain 3.5 g of stilbeneamine derivative of the formula (13-15) (yield: 77%, melting point: 153° C.), except that 0.017 mol (1.9 g) of 3-formylthiophene was used instead of 2-formylthiophene. The infrared absorption spectrum of the compound is shown in FIG. 3.

Comparative Synthesis Example 1

The same procedure as in Synthesis Example 4 was taken to obtain 0.0091 mol (4.9 g) of 4-phosphodiethylstyryl-2'-phenyl-6'-methyltriphenylamine, except that 0.0096 mol (4.7 g) of 4-chloromethylstyryl-2'-phenyl-6'-methyltriphenylamine was used instead of N,N-(4-chloromethylstyryl)diphenyl-1-naphthylamine.

Subsequently, the resultant compound was reacted with 0.011 mol (1.2 g) of benzaldehyde, instead of 2-formylthiophene, the same way as in Synthesis Example 1. Thus was obtained 3.8 g of stilbeneamine derivative represented by a formula (2-1) (yield: 80%).

(2-1)

Comparative Synthesis Example 2

The same procedure as in Synthesis Example 3 was taken to obtain 4.3 g of stilbeneamine derivative represented by a formula (3-1) (yield: 70%), except that 0.017 mol (1.9 g) of 2-formylthiophene was used instead of 3-formylthiophene.

(3-1)

Comparative Synthesis Example 3

The same procedure as in Synthesis Example 3 was taken to obtain 5.4 g of stilbeneamine derivative represented by a formula (4-1) (yield: 73%), except that 0.017 mol (3.3 g) of 6-formyl-2,2'-bithiophene was used instead of 3-formylthiophene.

(4-1)

Example 1

A ball mill was operated for 50 hours for mixing and dispersing 50 parts by weight of stilbeneamine derivative of the formula (12-2) synthesized in Synthesis Example 1 as the hole transport material; 5 parts by weight of X-type metal-free phthalocyanine (CG-1); and 100 parts by weight of polycarbonate in 800 parts by weight of tetrahydrofuran, thereby to prepare a coating solution for single-layer photosensitive layer.

Subsequently, the resultant coating solution was dip coated on an aluminum tube and then was air dried at 100° C. for 30 minutes. Thus was fabricated an electrophotosensitive material with a single-layer photosensitive layer having a thickness of 25 μm.

Example 2

An electrophotosensitive material with a single-layer photosensitive layer having a thickness of 25 μm was fabricated the same way as in Example 1, except that 50 parts by weight of stilbeneamine derivative of the formula (12-8) synthesized in Synthesis Example 2 was used as the hole transport material.

Example 3

An electrophotosensitive material with a single-layer photosensitive layer having a thickness of 25 μm was fabricated the same way as in Example 1, except that 50 parts by weight of stilbeneamine derivative of the formula (12-15) synthesized in Synthesis Example 3 was used as the hole transport material.

Example 4

An electrophotosensitive material with a single-layer photosensitive layer having a thickness of 25 μm was fabricated the same way as in Example 1, except that 50 parts by weight of stilbeneamine derivative of the formula (11-6) synthesized in Synthesis Example 4 was used as the hole transport material.

Example 5

An electrophotosensitive material with a single-layer photosensitive layer having a thickness of 25 μm was fabricated the same way as in Example 1, except that 50 parts by weight of stilbeneamine derivative of the formula (11-7) synthesized in Synthesis Example 5 was used as the hole transport material.

Example 6

An electrophotosensitive material with a single-layer photosensitive layer having a thickness of 25 μm was fabricated the same way as in Example 1, except that 50 parts by weight of stilbeneamine derivative of the formula (11-8) synthesized in Synthesis Example 6 was used as the hole transport material.

Example 7

An electrophotosensitive material with a single-layer photosensitive layer having a thickness of 25 μm was fabricated the same way as in Example 1, except that 50 parts by weight of stilbeneamine derivative of the formula (13-15) synthesized in Synthesis Example 7 was used as the hole transport material.

Comparative Example 1

An electrophotosensitive material with a single-layer photosensitive layer having a thickness of 25 μm was fabricated the same way as in Example 1, except that 50 parts by weight of stilbeneamine derivative of the formula (2-1) synthesized in Comparative Synthesis Example 1 was used as the hole transport material.

Comparative Example 2

An electrophotosensitive material with a single-layer photosensitive layer having a thickness of 25 μm was fabricated the same way as in Example 1, except that 50 parts by weight of stilbeneamine derivative of the formula (3-1) synthesized in Comparative Synthesis Example 2 was used as the hole transport material.

Comparative Example 3

An electrophotosensitive material with a single-layer photosensitive layer having a thickness of 25 μm was fabricated the same way as in Example 1, except that 50 parts by weight of stilbeneamine derivative of the formula (4-1) synthesized in Comparative Synthesis Example 3 was used as the hole transport material.

Electrical Characteristics Test

Each of the electrophotosensitive materials of the above examples and comparative examples was charged at +700±20V and the surface potential $V_0(V)$ thereof was measured using a drum sensitivity tester available from GENTEC Co.

A bandpass filter was used to extract monochromatic light from white light from a halogen lamp as a light source of the tester. The surface of the above electrophotosensitive material was irradiated with the extracted monochromatic light (light intensity I=16 μW/cm$^2$) having a wavelength of 780 nm and a half width of 20 nm for 80 msec while the half-life exposure $E_{1/2}$ (μJ/cm$^2$) was determined by measuring the time elapsed to the surface potential $V_0(V)$ decreased to half.

Subsequently, each of the electrophotosensitive materials was subjected to the above charging and light exposure processes repeated in 1000 cycles and then was determined for the half-life exposure $E_{1/2}$ (μJ/cm$^2$) at the 1000-th cycle.

The results are listed in Table 1.

TABLE 1

| | | $E_{1/2}$ | |
| --- | --- | --- | --- |
| | HTM | Initial | At 1000th cycle |
| EX. 1 | 12–2 | 0.59 | 0.60 |
| EX. 2 | 12–8 | 0.60 | 0.61 |
| EX. 3 | 12–15 | 0.57 | 0.61 |
| EX. 4 | 11–6 | 0.55 | 0.56 |
| EX. 5 | 11–7 | 0.53 | 0.55 |
| EX. 6 | 11–8 | 0.51 | 0.54 |
| EX. 7 | 13–15 | 0.57 | 0.58 |
| C. EX. 1 | 2–1 | 0.81 | 0.83 |
| C. EX. 2 | 3–1 | 0.68 | 0.75 |
| C. EX. 3 | 3–3 | 0.65 | 0.72 |

As seen from Table 1, the electrophotosensitive materials of Examples 1 to 7 have smaller initial half-life exposures and smaller half-life exposures after 1000 exposure cycles, as compared with the electrophotosensitive materials of Comparative Examples 1 to 3 using the prior-art stilbeneamine derivatives. This demonstrates that the electrophotosensitive materials of the invention achieve high photosensitivity and good repeatability.

This application is based on application No. 2001-080513 filed in Japan, the content of which is incorporated hereinto by reference.

What is claimed is:

1. An electrophotosensitive material comprising a photosensitive layer formed on a conductive substrate and containing a stilbeneamine derivative, as a hole transport material, represented by a formula selected from the group consisting of:

(11)

(12)

-continued

(13)

and mixtures thereof, wherein $R^1$ denotes an alkyl group, alkoxy group, aryl group, aralkyl group, halogen atom or hydrogen atom; $Ar^1$ and $Ar^2$ are the same or different, each denoting an aryl group; $Ar^3$ denotes an arylene group; and $Ar^4$ denotes an arylene group or divalent heterocyclic group.

2. The electrophotosensitive material according to claim 1, wherein said photosensitive layer is a single-layer photosensitive layer containing a binder resin, a charge generating material and said transport material.

3. The electrophotosensitive material according to claim 1, wherein said photosensitive layer is a multi-layer photosensitive layer comprising a charge generating layer and a charge transport layer laminated, the charge generating layer containing a charge generating material, and the charge transport layer containing a binder resin and said transport material.

4. A stilbeneamine derivative represented by a formula (11):

(11)

wherein $R^1$ denotes an alkyl group, alkoxy group, aryl group, aralkyl group, halogen atom or hydrogen atom; $Ar^1$ and $Ar^2$ are the same or different, each denoting an aryl group; $Ar^3$ denotes an arylene group; and $Ar^4$ denotes an arylene group or divalent heterocyclic group.

5. A stilbeneamine derivative represented by a formula (12):

(12)

wherein $R^1$ denotes an alkyl group, alkoxy group, aryl group, aralkyl group, halogen atom or hydrogen atom; $Ar^1$ and $Ar^2$ are the same or different, each denoting an aryl group; and $Ar^3$ denotes an arylene group.

6. The A stilbeneamine derivative represented by a formula (13):

(13)

wherein $R^1$ denotes an alkyl group, alkoxy group, aryl group, aralkyl group, halogen atom or hydrogen atom; $Ar^1$ and $Ar^2$ are the same or different, each denoting an aryl group; $Ar^3$ denotes an arylene group; and $Ar^4$ denotes an arylene group or divalent heterocyclic group.

* * * * *